United States Patent [19]

Redington et al.

[11] 4,015,836
[45] Apr. 5, 1977

[54] MAMMOGRAPHY TABLE

[75] Inventors: Rowland W. Redington, Schenectady; John L. Henkes, Jr., Latham, both of N.Y.

[73] Assignee: General Electric Company, Schenectady, N.Y.

[22] Filed: Jan. 16, 1976

[21] Appl. No.: 649,707

Related U.S. Application Data

[62] Division of Ser. No. 600,874, July 31, 1975.

[52] U.S. Cl. .............................................. 269/322
[51] Int. Cl.² ......................................... A61G 13/00
[58] Field of Search .................... 269/322–328; 250/439, 444, 445, 445 T, 446, 447, 448, 449, 450, 451, 456, 510, 320, 321, 322, 323

[56] References Cited
UNITED STATES PATENTS

| | | | |
|---|---|---|---|
| 1,925,425 | 9/1933 | Wilent | 269/323 |
| 2,103,693 | 12/1937 | Pohl | 269/323 |
| 3,226,106 | 12/1965 | Johnson et al. | 269/325 |
| 3,806,109 | 4/1974 | Weber | 269/323 |

*Primary Examiner*—Al Lawrence Smith
*Assistant Examiner*—Robert C. Watson
*Attorney, Agent, or Firm*—Jack E. Haken; Joseph T. Cohen; Jerome C. Squillaro

[57] ABSTRACT

A mammography machine for examination of a pendant breast contained in a fluid transmission medium. Patient support is provided at the upper rib cage, lower rib cage, and the shoulder adjacent the breast undergoing examination. X-ray scans are accomplished by rotation about a vertical axis extending through the pendant breast.

Patient loading is facilitated by a fabric sling rotatably affixed about a horizontal axis adjacent the lower body of the patient.

8 Claims, 5 Drawing Figures

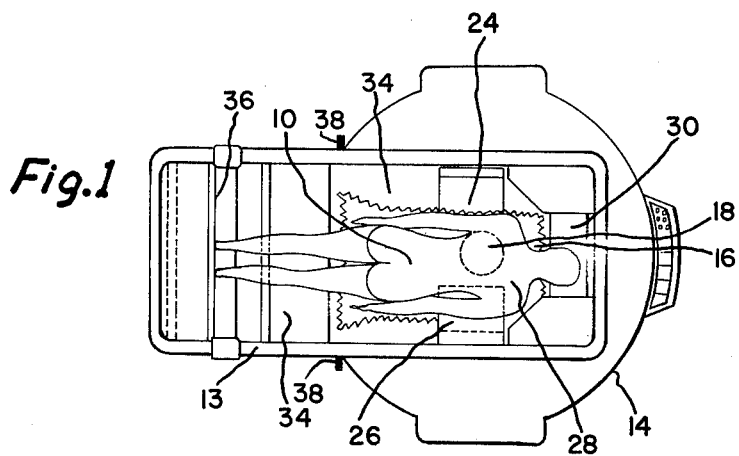
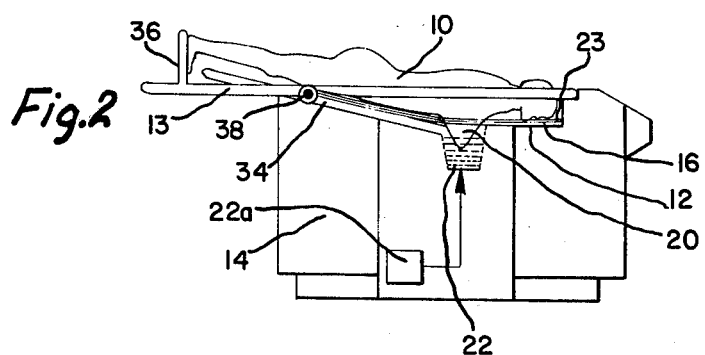
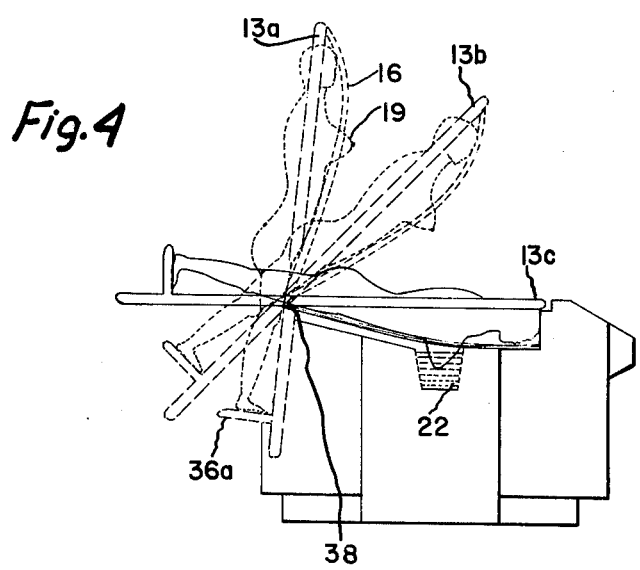

MAMMOGRAPHY TABLE

This is a division of application Ser. No. 600,874, filed July 31, 1975.

BACKGROUND OF THE INVENTION

This invention concerns equipment and methods for x-ray mammography. More specifically this invention concerns equipment and methods for positioning and supporting patients during tomographic mammography procedures.

Cancer of the breast is a major cause of death among the American female population. Effective treatment of this desease is most readily accomplished following early detection of malignant tumors. Major efforts are presently under way to provide mass screening of the population for symptoms of breast tumors. Such screening efforts will require sophisticated, automated equipment to reliably accomplish the detection process.

The x-ray absorption density resolution of present photographic x-ray methods is insufficient to provide reliable early detection of malignant breast tumors. Research has indicated that the probability of metastatis increases sharply for breast tumors over 1 cm in size. Tumors of this size rarely produce sufficient contrast in a mammogram to be detectable. To produce detectable contrast in photographic mammograms 2 to 3 cm dimensions are required. Calcium deposits used for inferential detection of tumors in conventional mammography also appear to be associated with tumors of large size. For those reasons, photographic mammography has been relatively ineffective in the detection of this condition.

A method of computerized x-ray tomography has recently been developed which is capable of providing greatly increased sensitivity for the detection of tumors in soft tissue. Variations of tomographic x-ray methods have, for example, been described in U.S. Pat. Nos. 3,778,614 and 3,881,110 to Hounsfield and others. The method generally involves the electrical detection and recording of a plurality of x-ray views taken along multiple transmission paths through tissue. The views are then combined in suitable computing machinery to provide detailed cross sections of the internal tissue structure.

The calculation of image data from tomographic information is greatly simplified if the x-ray absorbtion along the various transmission paths is approximately equal. It has, therefore, been a common practice to immerse tissue undergoing tomographic examination in a symmetrical mass of fluid. The above-referenced Hounsfield U.S. Pat. No. 3,881,110 describes a structure for immersing body parts in such a fluid.

The time required for mammographic x-ray exposures may be substantially reduced by use of a diverging x-ray beam and a multiple detector array. The efficient calculation of image information produced in such a configuration, however, requires that views be taken about a 360° arc surrounding the tissue.

Approximately 50 percent of breast tumors are known to occur in the upper, outer quadrant of the breast. A significant number of breast tumors also occur within approximately 1 cm of the skin. Prior art mammographic methods were generally inadequate to detect these tumors.

SUMMARY OF THE INVENTION

In accordance with the present invention we provide structures and methods for conducting mammographic examination upon the downwardly extending, pendant breast of a prone patient. The rib cage, shoulder, and head of the patient are supported on a horizontal table. The breast extends downward, through an aperture in the table, into a fluid-filled container. An x-ray source and tomographic detector rotate about a vertical axis extending through the breast. A three-point support on the upper rib cage, lower rib cage, and shoulder provides maximum extension of the tail and axilla into the fluid. The fluid in contact with the skin allows high density resolution in adjoining tissues to permit accurate detection of tumors in that region.

A patient handling structure is rotatable about a horizontal axis to permit fast and effortless loading and positioning. The handling structure comprises a fabric sling which provides uniform support and minimizes pinching effects as the patient is brought into contact with the above-described horizontal table.

It is, therefore, an object of this invention to provide structures for supporting a patient during tomographic examination of the breasts.

Another object of this invention is to provide structures for maximizing the volume of tissue scanned during tomographic mammography.

Another object of the invention is to provide structures and methods for fast and efficient screening of potential breast cancer victims.

Another object of this invention is to provide a patient handling mechanism for rapid and easy loading of a patient on an examination table, with provision for convenient and accurate positioning of the patient.

Yet another object of the invention is to provide structures and methods for increasing the x-ray absorption density resolution and the detection probability during breast cancer examination.

BRIEF DESCRIPTION OF THE DRAWINGS

The novel features believed to be characteristic of the present invention are set forth in the appended claims. The invention itself, together with further objectives and advantages thereof, may best be understood with reference to the following detailed descriptions, taken in connection with the appended drawings in which:

FIG. 1 is a top view of a tomography machine of the present invention;

FIG. 2 is a sectional side view of the machine of FIG. 1;

FIG. 4 schematically illustrates the operation of a rotatable patient table in the machine of FIG. 1.

DESCRIPTION OF THE PREFERRED EMBODIMENT

Figure 5:
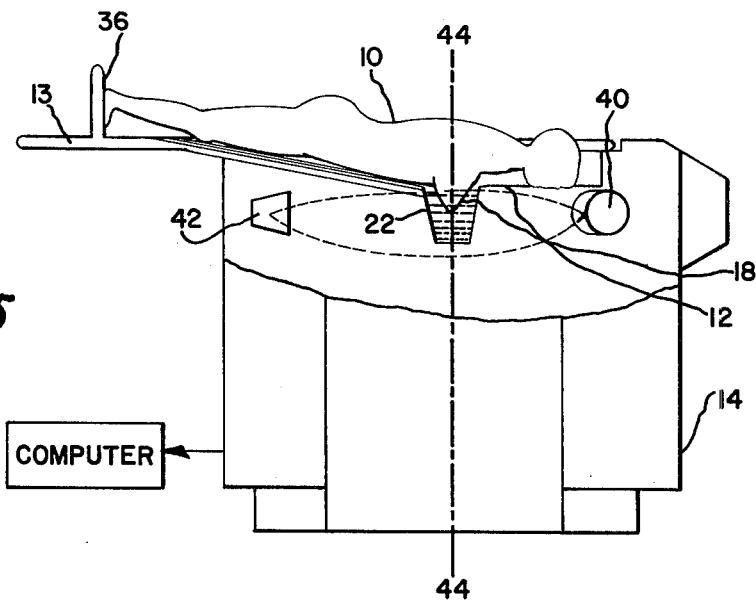
FIG. 5 is a sectional side view of the machine of FIG. 1 illustrating the motion of the x-ray source and detector.

X-ray tomographic images are reconstructed by convolving views taken along a plurality of transmission paths in a plane passing through the object undergoing investigation. The transmission of x-rays through an image element in the plane is derived from computations upon the transmission characteristics along paths passing through that element. The absorption of x-rays is logarithmic in nature so that any element containing a strong absorption gradient may produce significantly different computed values for measurements along different paths. This condition, which results in significant errors during imaging of tissue density distributions, is particularly pronounced at an air-tissue interface.

We have determined, by calculation and experiment, that a practical tomographic system will be incapable of resolving tumors in soft tissue in the region of a tissue-air interface. This effect is relatively unimportant in the case of substantially cylindrical structures, for example, the torso of a human body; but introduces significant errors of resolution during the examination of a conical structure, such as is encountered in mammographic examination. We have, therefore, concluded that a breast undergoing tomographic examination should preferably be surrounded with a medium having an x-ray absorption coefficient which is relatively close to that of soft human tissue. Water is such a medium.

We have determined that tomographic examination of the breast may be most readily carried out upon a prone patient with the breast pendantly extending into a water-filled container. Medical data indicates that upward of 50 percent of all breast tumors occur in the upper, outer quadrant which is predominately the axilla and the tail of the breast. Effective screening for breast tumors therefore mandates that these structures be included in the examination.

Our investigations have indicated that the axilla and tail of the breast are most suitably presented for examination in a prone patient supported at the lower rib cage, the shoulder nearest the breast undergoing examination and the upper rib cage adjacent the opposite breast. The adjacent arm is carried at the side of the torso allowing maximum extension of the axilla into the measurement system. A tomographic scan through a horizontal plane in the breast tissue is then performed by rotating an x-ray source and detector assembly about an axis extending vertically through the pendant breast. Successive planes are scanned by translating the detector and source vertically to produce a composite, three-dimensional image of the breast tissue structure.

Prior art x-ray photographic mammography of pendant breasts has been reported; notably by Lasky in *Radiology*, Vol. 91, August 1968 and more recently at the University of Michigan Cancer Center. These reports involve conventional exposure of photographic film however, and consequently do not consider the need for a fluid medium or the problems associated with tomographic scans. The novel features of applicants' invention, are directed toward patient handling and support structures and toward methods for the tomographic examination of pendant breasts which are suspended in a fluid medium.

Figure 3:
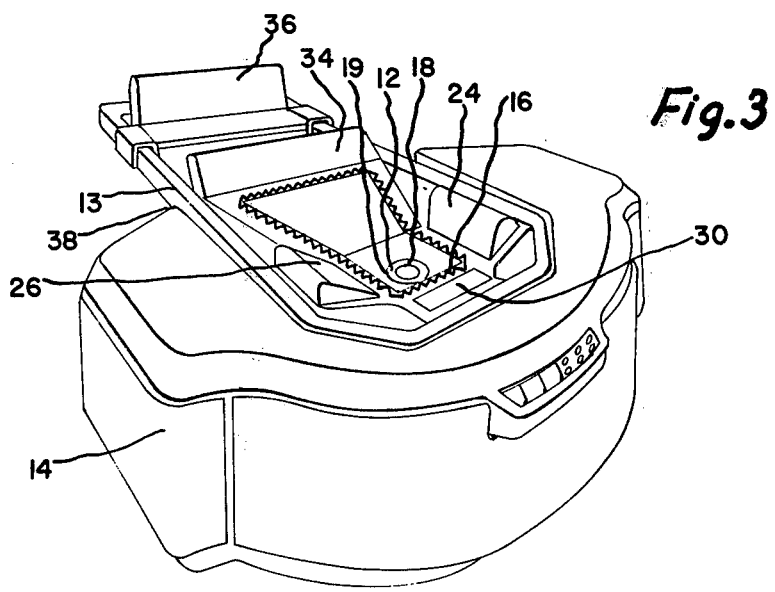
FIG. 3 is a perspective view of the machine of FIG. 1.

FIGS. 1, 2, and 3 are illustrative of a machine for supporting and positioning a patient during tomographic mammography procedures. A patient 10 is supported in prone position on a horizontal table structure 12 which is disposed at the top of a support and enclosure assembly 14. The table surface is perforated by a round opening 18 which is adapted to permit passage of the breast 20. The breast 20 extends pendantly through the opening 18 into a fluid-filled container 22. The fluid is selected to provide an x-ray absorption coefficient substantially equal to that of soft human tissue and may, for example, comprise water combined with suitable surfactants and chemical additives to minimize bubble formation and foaming within the container 22. The water is ideally maintained near body temperature and may be outgassed by boiling under vacuum conditions, in a chamber 22a, before insertion into the container 22.

A fabric sling 16 supports the patient 10 during loading and positioning procedures and minimizes pinching effects which might otherwise occur when the patient 10 contacts the rigid table structure 12. The sling extends under the rib cage of the patient and is perforated by a substantially round opening 19 aligned over the above-described opening 18 in the table surface 12. The sling is supported by a rotatable loading frame 13 (more fully described below) and may be constructed from canvas, nylon, or any other fabric which may be readily cleaned and sterilized. A disposable pad 23 (FIG. 2) which may, for example, be paper may be placed between the patient 10 and the sling 16 to ensure cleanliness.

A pair of adjustable triangular cushions 24 and 26 are disposed on the frame 13 laterally adjacent the sling 16 to support the upper rib cage of the patient 28 opposite the breast undergoing examination. The cushions 24 and 26 are symmetrically disposed about the examination openings 18 and 19 to permit lateral shifting of the patient for rapid alternate examination of the breasts. A relatively rigid support surface 30 extends forward from the sling 16 to support the head of the patient. Our investigations have determined that the axilla and tail of the breast may be most advantageously presented through the opening 18 by use of this three point support system which provides support under the upper opposite and lower adjacent rib cage and at the adjacent shoulder of the patient.

A substantially rigid platform 34 extends backward and upward from frame 13 to support the hips and thighs of the patient. Platform 34 most advantageously forms an angle of approximately 15° with the horizontal plane to permit clearance for the x-ray tomographic equipment within the enclosure 14 with maximum patient comfort.

An adjustable footrest 36 extends upward from the frame structure 12 in the region behind the sloping platform 34. The footrest may be readily translated along the length of the frame 13 and clamped in position to accommodate patients of varying height.

To facilitate the rapid loading and positioning of the patient, the frame 13 is rotatable about a horizontal axis 38 at the rear of the enclosure 14. FIG. 4 schematically illustrates the manner of patient loading (portions of the structure are omitted for clarity). The frame structure is raised to near vertical position 13a. The patient enters the machine by stepping onto the footrest 36a and leaning against the sling 16 with the breast extending through the opening 19. The frame is then rotated to an intermediate position 13b whereat the proper positioning of patient on the sling, cushions, and head rest may be verified by the machine operator. The frame is then further lowered to a horizontal position 13c whereat the pendant breast extends downwardly into the fluid container 22.

In the sectional view of FIG. 5, an x-ray source 40 and an electronic x-ray detector array 42 are disposed on opposite sides of the fluid container 22 within the enclosure 14. Means are provided for rotating the x-ray source 40 and the detector array 42 about a vertical axis 44 extending through the fluid container 22 and the opening 18. Information from repetitive tomographic views of the breast is collected as the detector 42 and the source 40 rotate 360° about the axis 44 and is transmitted to a computer 46 for the reconstruction of tissue images. The x-ray source 40 and the detector 42 may be translated vertically along the axis 44 to provide successive views through adjacent horizontal planes in the pendant breast tissue.

The structures and methods of the present invention allow rapid and comfortable patient positioning and support during tomographic mammography procedures. The structures maximize the area of the breast, tail, and axilla presented for examination and are readily adaptable to the use of fluid transmission media. The shape of the structures and the positioning of the patient allow the detector and X-ray source to rotate 360° around the axis of the breast undergoing examination to permit the use of relatively simple image reconstruction algorithms and a divergent beam x-ray geometry.

The invention has been described in detail herein in accord with certain embodiments thereof, yet many modifications and changes therein may be effected by those skilled in the art. Accordingly, it is intended by the appended claims to cover all such modifications and changes as fall within the true spirit and scope of the invention.

The invention claimed is:

1. A tomographic examination table comprising:
 a fabric sling horizontally disposed;
 shoulder and lower rib cage support means, including a horizontal surface, disposed below said sling which function to support the shoulder and lower rib cage of a female humoid patient;
 rigid platform means extending from said sling which function to support the lower body of said patient; and
 upper rib cage support means extending diagonally upwards from the sides of said sling.

2. The table of claim 1 wherein said platform means extend diagonally upwards from said surface at an angle of approximately 15° with the horizontal plane.

3. The table of claim 2 wherein said upper rib cage support means are cushioned and wherein the position of said upper rib cage support means is adjustable.

4. The table of claim 2 wherein said sling and said surface are perforated to define aligned openings.

5. The table of claim 1 further comprising rotatable support means adapted to allow rotation of said sling and said rigid platform means about a horizontal axis.

6. The table of claim 5 further comprising footrest means extending from the platform means and forming a substantially right angle with said sling whereby a standing patient is supported by said table.

7. The table of claim 6 further comprising means for rotating said platform means and said sling about said axis.

8. The table of claim 7 wherein a mamma of said patient extends pendantly downward through said aligned openings.

* * * * *